(12) United States Patent
Nabhan

(10) Patent No.: US 10,129,450 B2
(45) Date of Patent: Nov. 13, 2018

(54) SYSTEM AND METHOD FOR OPHTHALMOLOGICAL IMAGING ADAPTED TO A MOBILE PROCESSING DEVICE

(71) Applicant: Tareq Issam Nabhan, Bridgeton, MO (US)

(72) Inventor: Tareq Issam Nabhan, Bridgeton, MO (US)

( * ) Notice: Subject to any disclaimer, the term of this patent is extended or adjusted under 35 U.S.C. 154(b) by 85 days.

(21) Appl. No.: 15/283,380

(22) Filed: Oct. 1, 2016

(65) Prior Publication Data

US 2018/0092534 A1  Apr. 5, 2018

Related U.S. Application Data

(60) Provisional application No. 62/236,841, filed on Oct. 2, 2015.

(51) Int. Cl.
*A61B 3/14* (2006.01)
*H04N 5/225* (2006.01)
(Continued)

(52) U.S. Cl.
CPC ......... *H04N 5/2257* (2013.01); *A61B 3/0025* (2013.01); *A61B 3/0041* (2013.01);
(Continued)

(58) Field of Classification Search
CPC ....... A61B 3/14; A61B 3/0008; A61B 3/1208; A61B 3/101
(Continued)

(56) References Cited

U.S. PATENT DOCUMENTS

| 7,467,870 B2 * | 12/2008 | van de Kraats | ..... A61B 3/1176 |
| | | | 351/206 |
| 7,661,820 B2 * | 2/2010 | Hara | ..... A61B 3/101 |
| | | | 351/206 |

(Continued)

*Primary Examiner* — Mahidere Sahle

(57) ABSTRACT

A system and method for ophthalmological imaging is provided for use with a mobile processing device, wherein the mobile processing device comprises a camera lens, light source, and processor configured to process images captured, received, and/or delivered by the mobile processing device. The mobile processing device adapted ophthalmological instrument system comprises housing segments, circuitry, lights, and a frustum cone, wherein the frustum cone comprises reference lines of a plurality of circular, frustoconical, alternating transparent and opaque concentric rings in the conical surface in optical alignment with the mobile processing device's camera lens and subject's central cornea and/or tear-film layer(s). Reflections of the reference lines off the cornea and/or tear-film layer are imaged by the mobile processing device and analyzed by software applications downloaded to and/or accessed by the smart-phone's processor(s), wherein data of shape, structure, composition, function, and/or power of the cornea and/or tear-film layer(s) are determined by methods comprising one or more image processing and/or computer vision functions configured to produce topographic data. The processor of the mobile processing device can provide and/or receive specific information to/from other instruments and/or users through a communications network.

45 Claims, 9 Drawing Sheets

(51) Int. Cl.
  *A61B 3/00* (2006.01)
  *G16H 30/40* (2018.01)
  *G16H 30/20* (2018.01)
  *G16H 50/20* (2018.01)
(52) U.S. Cl.
  CPC ............... *A61B 3/14* (2013.01); *G16H 30/20* (2018.01); *G16H 30/40* (2018.01); *G16H 50/20* (2018.01); *H04N 5/2254* (2013.01); *H04N 5/2256* (2013.01)
(58) Field of Classification Search
  USPC .................................................. 351/206, 208
  See application file for complete search history.

(56) References Cited

U.S. PATENT DOCUMENTS

2012/0050683 A1* 3/2012 Yates ................... A61B 3/1208
                                                            351/219
2013/0128223 A1* 5/2013 Wood ..................... A61B 1/227
                                                            351/206

* cited by examiner

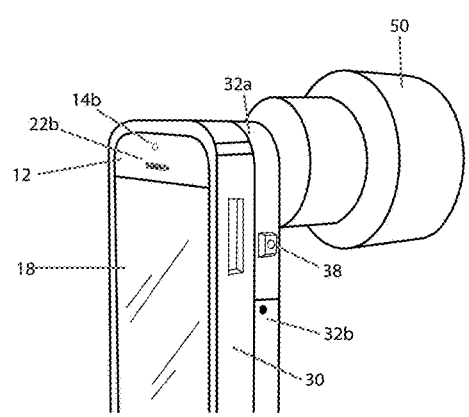
Fig.10 -A
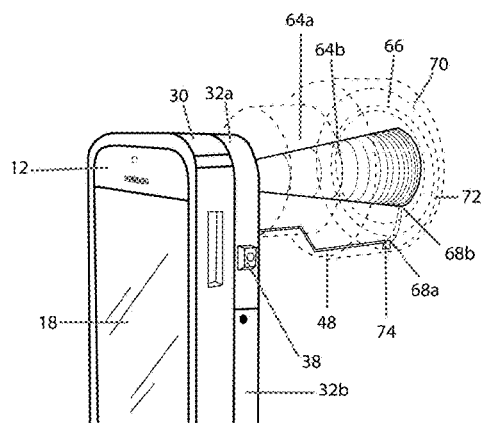
Fig.10 -B
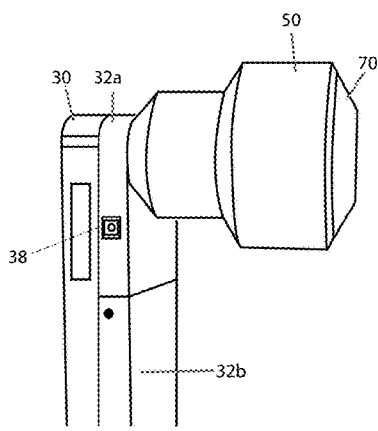
Fig.11 -A
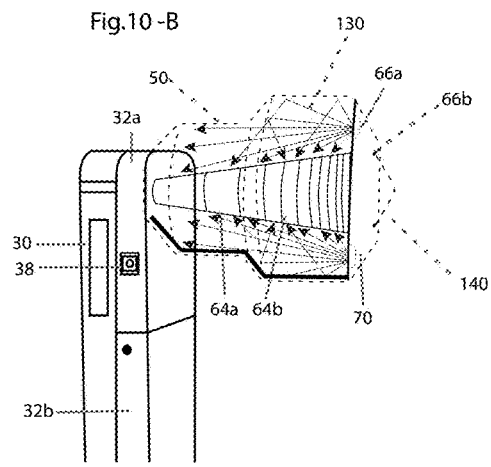
Fig.11 -B

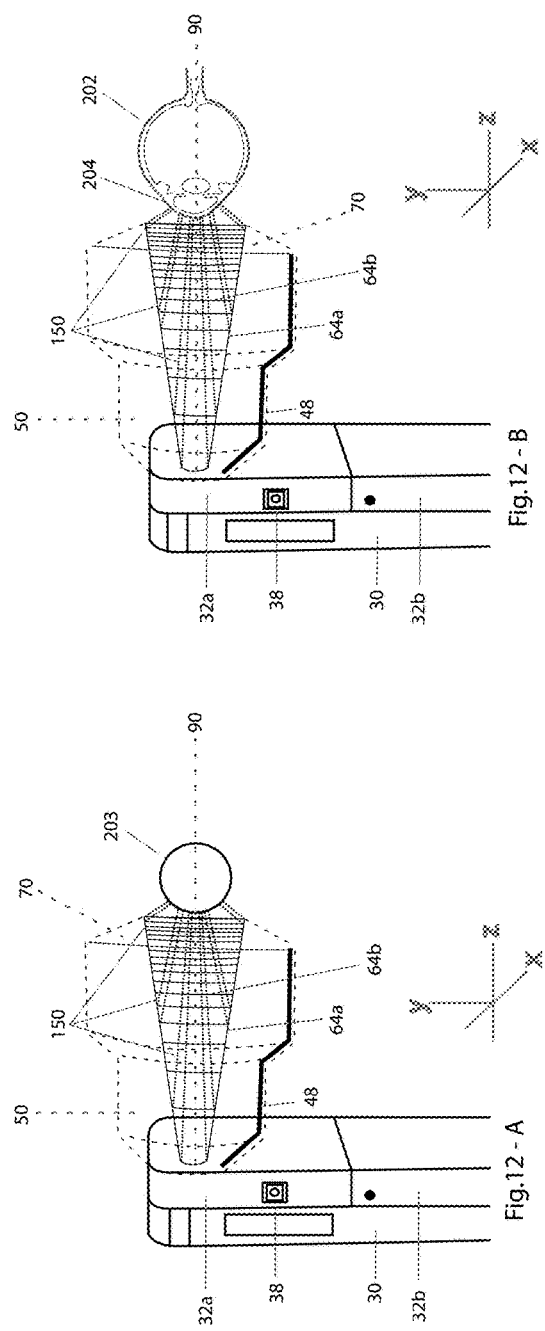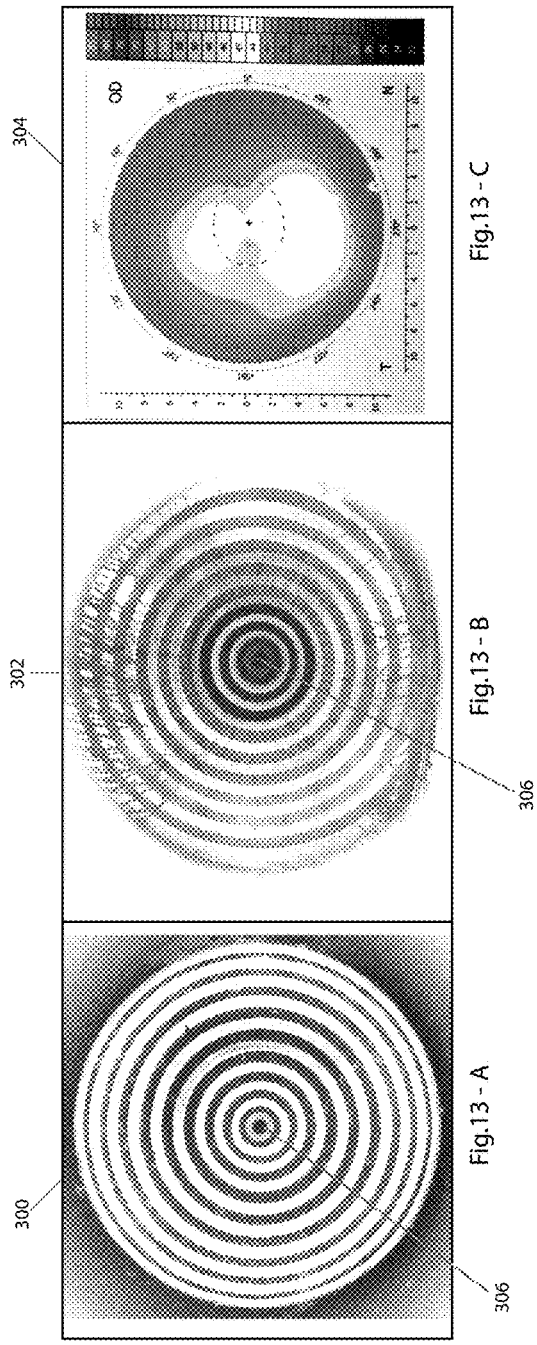

SYSTEM AND METHOD FOR OPHTHALMOLOGICAL IMAGING ADAPTED TO A MOBILE PROCESSING DEVICE

CROSS-REFERENCE TO RELATED APPLICATIONS

This application claims priority to U.S. Provisional Application Ser. No. 62/236,841 filed on Oct. 2, 2015 which is hereby incorporated by reference.

STATEMENT REGARDING FEDERALLY SPONSORED RESEARCH

Not Applicable

APPENDIX

Not Applicable

I. BACKGROUND OF THE INVENTION

1. Field of the Invention

The present invention comprises a system and method for obtaining, measuring, analyzing, translating, and/or interpreting captured and/or received and/or delivered, qualitative and/or quantitative parameters of a surface(s) and/or layer(s) and, in particular, concerning a corneal topography system and method that is adapted to a mobile processing device.

2. Related Art

It is understood that the shape of the cornea accounts for approximately two-thirds of the eye's total optical power and that disturbances in its shape contribute to changes in the eye's refractive status. The cornea substantially contributes to an eye exhibiting either emmetropia or ametropia, wherein an emmetropic eye manifests without refractive error; in other words, a normal refraction of light rays by an eye. An ametropic eye is an eye that comprises nearsightedness (myopia), farsightedness (hypermetropia/hyperopia), and/or possess different powers in different meridians and/or axes (astigmatism); in other words, a faulty refraction of light rays by the eye. Such variations in shape result in incident light rays being defracted to establish focal point(s) in front of the retina, on the retina, behind the retina, and/or in combinations thereof. As a consequence, the cornea is a source of focus for a plethora of surgical techniques and for contact lens and spectacle corrections. It is appreciated that detailed corneal information is essential to properly diagnose and treat patients, and that the advent of corneal topography serves in this capacity. Corneal topographers are instruments used to measure the anterior, and sometimes posterior, surface curvatures of the cornea. Most corneal topographers use a design that consists of a series of concentric circles of alternating black and white rings known as the Placido disk. In 1880, Portuguese ophthalmologist Antonio Placido, viewed the reflections of a painted flat disk of alternating black and white rings from the cornea and deduced that the reflected contour line patterns indicate a shape and power of the eye. More advanced corneal topographers are conically shaped to slightly parallel the convexity of the cornea and are illuminated so as to project the rings onto the cornea (as in U.S. Pat. No. 5,526,073). The reflected ring patterns and any disturbances and/or deformations to the concentric ring contours are captured by photography and/or videography through the center of the disk and reconstructed with large, expensive, non-portable hardware and software to generate a corneal topography. Attempts have been made to make corneal topography a more portable tool (as in U.S. Pat. No. 6,152,565) yet still resting on the computational power of a separate computer system. A more recent attempt utilized a flat panel display wherein the display projects markings onto the cornea (as in U.S. Pat. No. 2016/0000322 A1). No such systems have been linked with mobile processing device technology for image capture, image reception, image delivery, image processing, and/or telemedicine. Furthermore, no such systems perform image analysis and/or generate topographic constructs and/or reconstructs comprising a mobile processing device and its camera lens(es) and/or processor(s) via methods of image processing and/or computer vision and/or scene understanding functions.

3. Telemedicine

Telemedicine is basically defined as remote diagnosis and treatment of patients by means of telecommunications technology. Mobile processing devices, specifically smart-phones, are an unparalleled aspect of telemedicine and are currently being used as sophisticated medical devices. Global mobile-cellular subscriptions have grown to nearly 7 billion in 2014 and 90% of healthcare professionals report using a smart-phone in practice. With the high smart-phone penetration and rapidly growing global telecommunications infrastructure, mobile processing devices in telemedicine provide an unprecedented opportunity in healthcare. Hence, exploiting the existing smart-phone infrastructure to monitor and treat health conditions, and/or to conduct epidemiological health assessments, and/or in the arenas of basic and/or clinical research, serves as a low-cost healthcare method. In eye care alone there are nearly 350 ophthalmology/optometry-based applications, and according to scholarship, this is only the beginning of the uses of mobile processing device technology in eye care. Furthermore, the benefit of better patient care via accurate, more affordable and portable equipment, meets the criteria and/or procedural codes for managed care reimbursement(s).

4. Market Economics

When considering the potential demand for a system and method for ophthalmological imaging adapted to a mobile processing device, it is most convenient to consider the clinical indications for corneal topography and to adapt the technology to a more affordable, portable, and ubiquitous device. Every ophthalmologic and optometric academic institution has at least one corneal topographer, and more and more clinical practitioners use topography in the management of their patients, however, cost has kept most independent eye care practitioners from purchasing corneal topographers. The present invention of a system and method for ophthalmological imaging adapted to a mobile processing device satisfies the medical and clinical standards of care, is unparalleled in outreach and research utility, and is economically advantageous.

5. Indications

Corneal topography is a critical tool used to assess and properly treat patients. The utility of corneal topography is to obtain refractive error values, to establish biometric parameters for laser refractive and implantable artificial lens surgeries, to aid in diagnosing, monitoring, and treating corneal dystrophies, to help practitioners properly fit soft, rigid, hybrid, and/or therapeutic/drug delivery contact lenses, and to accurately prescribe spectacle correction(s). Since more than 80% of all contact lens wearers report going to an optometrist, the present invention will benefit optometric clinicians, residents, and students in private practice(s), retail chains, health centers, and in academic institutions by offering a more affordable, practical, convenient, and ubiquitous option for corneal topography. More still, are ophthalmologic indications for corneal topography. Statistically, cataract surgery is of the top three most common ambulatory surgeries performed in the United States per year at over 3 million. Sadly, yet preventatively, cataracts are the leading cause of blindness in developing countries, accounting for 51% of all blind persons worldwide. Furthermore, nearly 1-million American persons per year are reported to have cosmetic corneal refractive surgery and over 1-million Americans have had a corneal transplant. Corneal disease is also a major cause of worldwide blindness. Since the majority of worldwide corneal blindness and vision impairment affect those of lower socio-economic standing, the preferred embodiment of the present invention of a system for ophthalmological imaging adapted to a mobile processing device and a method comprising a dedicated software system of image analysis by image processing and/or computer vision and/or scene understanding functions will have unparalleled institutional, clinical, and field potential. More indications of corneal topography include corneal cross-linking (CXL) and/or corneal reshaping technologies/orthokeratology (CRT/ortho-K). Nearly two in one thousand people are affected by keratoconus world-wide. According to The Cornea Research Foundation, CXL is at the forefront of keratoconus treatment. Its utility rests on serial corneal topographs and the treatment is pending FDA approval as the standard of care for the management of keratoconus. The medical standard of care indicates corneal topography for the millions of cataract, transplant, and refractive surgeries in the US alone. The portability and versatility of a system and method for ophthalmological imaging adapted to a mobile processing device would offer surgeons real-time and/or serial corneal topographs pre, peri, and post-operatively. A system and method for ophthalmological imaging adapted to a mobile processing device would also be the platform to collect, analyze, and publish novel, rapidly assessed epidemiologic studies. This invention is secondary to the plethora of research dedicated to making use of sophisticated mobile processing device technology (camera, light source, enhancements/editions, software applications) and linking it to bettering patient eye care, globally. The invention does not reinvent the topographer. The essence of the invention is to harness the novel utility of corneal topography via image processing and/or computer vision and/or scene understanding functions, and in the preferred embodiment, linking it to mobile processing devices with the criteria that topography, and topography via image processing and/or computer vision and/or scene understanding functions is non-obvious when linked to a mobile processing device(s). The indications for a system and method for ophthalmological imaging adapted to a mobile processing device is academically and clinically necessary and the market demand for a cheaper, convenient, versatile, effective, and ubiquitous tool has become paramount. Further areas of applicability of the present invention are apparent in the detailed description provided hereinafter. It should be understood that the detailed descriptions and specific examples, while indicating the preferred embodiment of the invention, are intended for the purposes of illustration only. They do not intend to limit the scope or utility of the invention.

II. OBJECT OF THE INVENTION

It is an object of the present invention to adapt a corneal topographer to a smart-phone and/or any mobile communications and/or computing device that operates as a photograph and/or video, hereinafter collectively referred to as image(s), capture and/or receiving and/or delivering device, hereinafter collectively defined as mobile processing device(s). Under the preferred embodiment, the high resolution camera features and/or functions, computing and/or processing power, storage volume, available and creatable applications, and/or communications potential of the smart-phone would allow for image capture, reception, and/or delivery of the reflected ring projections, construction, reception, and/or delivery of corneal topographies, and/or sharing of the information through a communications network(s). It is another object of the present invention to provide an easier and cheaper method of constructing corneal topography and to qualify and quantify corneal surface tear quality from the reflected ring patterns by using image processing and/or computer vision and/or scene understanding functions to analyze the reflected images captured, received, and/or delivered. In the preferred embodiment, software application(s) comprising algorithm(s) and/or operator(s) comprising one or more image processing and/or computer vision and/or scene understanding functions, is configured to produce qualitative (saturation, density, contrast, and/or color scaled) and/or quantitative (identified axes, radii of curvature, and/or dioptric power/magnitude of the corneal surface(s) and/or layer(s), and/or tear-film layer(s)) information and/or two dimensional and/or three dimensional map(s) and/or printings and/or topography(ies) and/or histogram(s) of a target source(s) and/or cornea(s) and/or tear-film layer(s).

In the preferred embodiment of the present invention, the advantages of a system and method for ophthalmological imaging comprising a mobile processing device compared to current technology includes an easier and cheaper method of corneal topographic image collection, capture, and/or analysis; adaptability to the ubiquity of smart-phones and/or other mobile processing devices; portability in outreach; utility for the mobility impaired, infant, and/or under anesthetic ocular examinations; utility in modular medicine; ease of network communications; and/or research applications. The application of this technology can have global epidemiological implications in rapid assessment studies of vision impairments and avoidable blindness initiatives. Furthermore, the utility in animal studies to generate models for human clinical trials are additional exemplary embodiments. More still, current topographers are large, expensive, and essentially non-mobile. This is a more affordable and more portable alternative to current corneal topographic systems. Other objects, advantages, and applications of the present invention will become apparent from the description in which embodiments of the present invention are described. It should be understood that the detailed description and specific examples, while indicating the preferred embodiment of the invention, are intended for purposes of illustration only and are not intended to limit the scope of the invention.

III. SUMMARY OF THE INVENTION

The present invention provides a system and method for ophthalmological imaging for use with a mobile processing device, wherein the mobile processing device comprises a camera lens(es), light source(es), and processor(s) configured to process images captured, received, and/or delivered by the mobile processing device. The mobile processing device adapted ophthalmological instrument system comprises a mobile processing device housing segment, circuitry and circuitry housing segment, a battery cover, a frustum cone housing segment, optimization lens(es), an optimization lens(es) and/or camera lens(es) tube, a frustum cone segment, ring-light(s), vertex-angulation positioning light(s), and a light(s) housing segment. The housing segments are capable of housing and/or partially housing respective units. The frustum cone segment comprises reference lines wherein an axial hole is provided and a plurality of circular, frusto-conical, alternating transparent and opaque, illuminated, concentric rings are provided in the conical surface about the hole in optical alignment with the mobile processing device's camera lens and subject's central cornea, and/or tear film layer(s), and/or target source. The vertex-angulation positioning light(s) are embedded within the mouth-end/distal-end walls of the frustum cone segment. The optimization lens(es) and lens tube are provided partially within the frustum cone and partially within the circuitry housing segment proximal to the camera lens(es) and in optical alignment with the frustum cone hole, the mobile processing device's camera lens, and the subject's central cornea, and/or tear-film layer(s), and/or target source. The mobile processing device adapted ophthalmological instrument system may be illuminated by the mobile processing device's own camera light source and/or preferably by a ring-light(s) embedded at the distal end of the frustum cone segment within the light(s) housing segment. The mobile processing device adapted ophthalmological instrument system is preferably used in combination with a smart-phone whereby the reflected plurality of concentric rings off the cornea, tear-film, and/or target source are captured, received, and/or delivered by the smart-phone camera lens(es) and/or media storage system(s) and processed by methods comprising image processing, computer vision, and/or scene understanding functions to determine data of shape, structure, composition, function, and/or power of the subject cornea(s), and/or tear-film layer(s), and/or target source(s). In the method of the invention this is provided by (a) positioning the eye on the optical axis; (b) illuminating the eye through the frustum cone segment having a center and center opening at the center through which the mobile processing device's camera lens(es) is situated, where the center being on the optical axis and the frustum cone segment having rings (Placido's disk) concentric about the optical axis; (c) observing and/or capturing an image of the Placido disk reflected from the eye along the optical axis, whereby the vertex-angulation light(s) are singularly focused and the entire and/or any portion of the cornea, and/or tear-film, and/or target source reflects images of the rings from the frustum cone segment spaced from the center.

The system and method for ophthalmologic imaging adapted to a mobile processing device comprises software applications downloaded to and/or accessed by the smart-phone's processor(s) to analyze captured, received, and/or delivered images of a subject's cornea, and/or tear-film layer(s), and/or target source and determine data of shape, structure, composition, function, state, and/or power of the subject cornea(s), and/or tear-film layer(s), and/or target source(s) by methods comprising algorithm(s) and/or operator(s) comprised of one or more image processing and/or computer vision functions configured to produce qualitative and/or quantitative information, two-dimensional and/or three-dimensional map(s), printings, topography(ies), and/or histogram(s) of subject cornea(s), and/or tear-film layer(s), and/or target source(s).

The processor(s) of the mobile processing device and/or dedicated server system(s) can provide specific information to other instruments and/or users and/or receive specific information from other instruments and/or users through a communications network(s).

Further areas of applicability of the present invention will become apparent from the detailed descriptions provided hereinafter. It should be understood that the detailed description and specific examples, while indicating the preferred embodiment of the invention, are intended for purposes of illustration only and are not intended to limit the scope of the invention.

IV. BRIEF DESCRIPTION OF THE DRAWINGS

The figures demonstrate the basis of the design and method of a system and method for ophthalmological imaging adapted to a mobile processing device, specifically the iPhone 5®. The figures/drawings constitute a part of the specification and include exemplary embodiments of the preferred embodied system and method for ophthalmological imagining adapted to a mobile processing device, which may be embodied in various forms, and are described by way of illustration and not by way of limitation. It is to be understood that in some instances various aspects of the invention are either magnified or minified and/or simplified and that to facilitate an understanding of the invention some figures are not necessarily to scale and/or detail.

Figure 3:
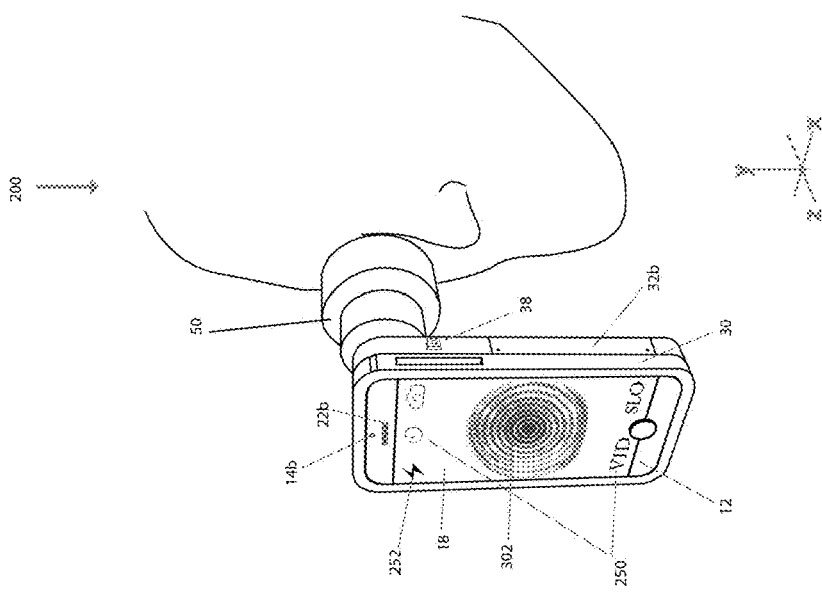
Figure 1:
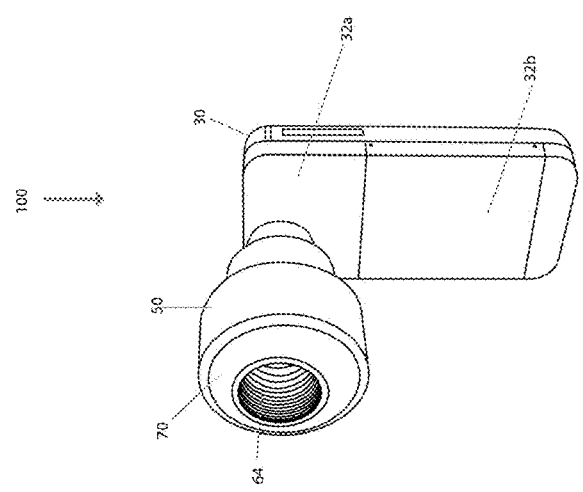
FIG. 1 is a perspective view illustrating the mobile processing device adapted ophthalmological instrument system.

FIG. 3 is a second perspective view of the imaging of a subject patient cornea and/or tear-film layer(s) and/or target source by the mobile processing device adapted ophthalmological instrument system of FIG. 1 coupled with a securely nestled mobile processing device (i.e. smart-phone) according to the present invention as it is used. Control menus for use with the smart-phone are also illustrated.

Figure 4:
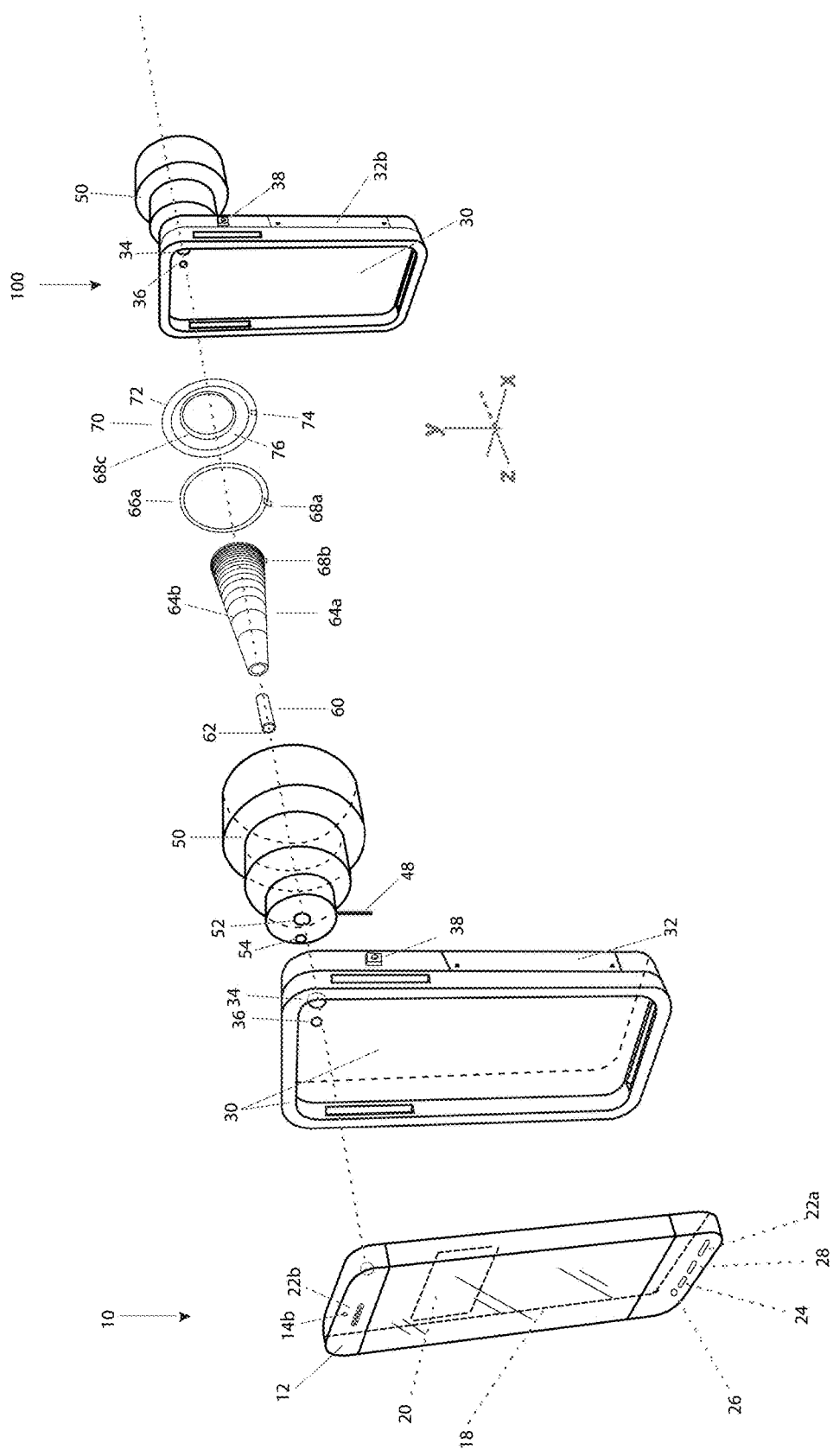

FIG. 4 is a second perspective view of a spaced-apart/exploded illustration of the segments of the mobile processing device adapted ophthalmological instrument system of FIG. 1.

Figure 5:
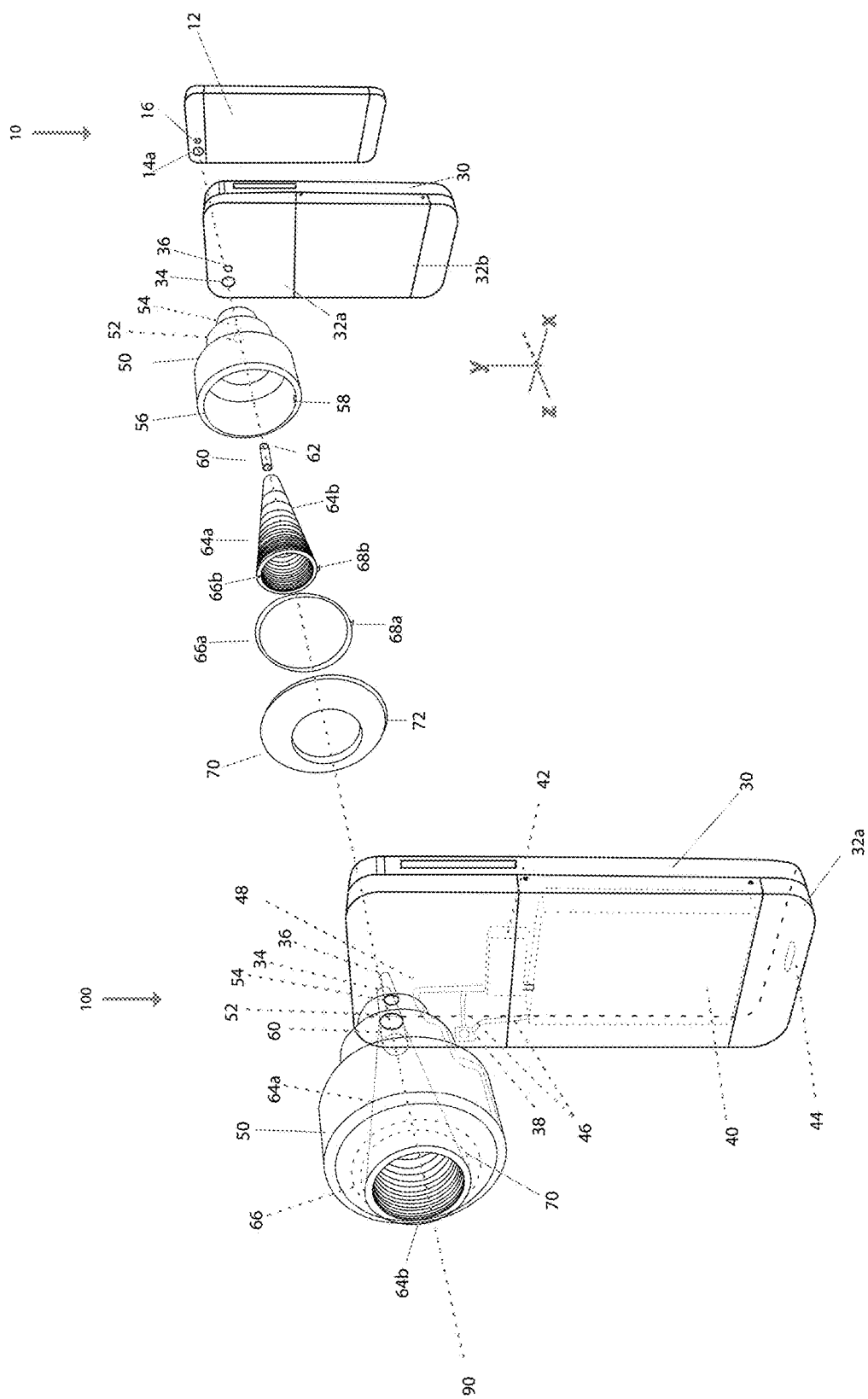

FIG. 5 is a perspective view of a spaced-apart/exploded illustration of the segments of the mobile processing device adapted ophthalmological instrument system of FIG. 1.

Figure 6:
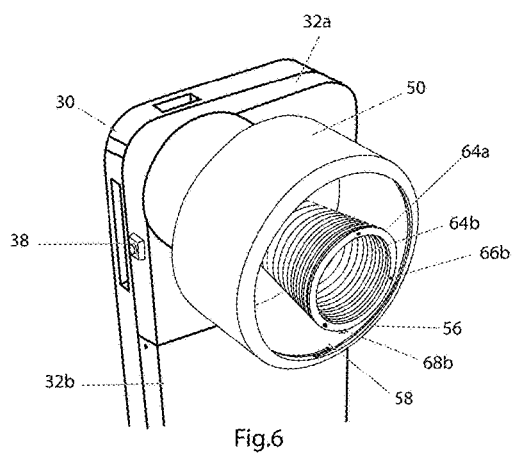

FIG. 6 is a third perspective view of the system with the ring-light and light housing segment removed illustrating the frustum cone position, vertex-angulation positioning light(s), and conduction lead within the frustum cone housing segment.

Figure 7:
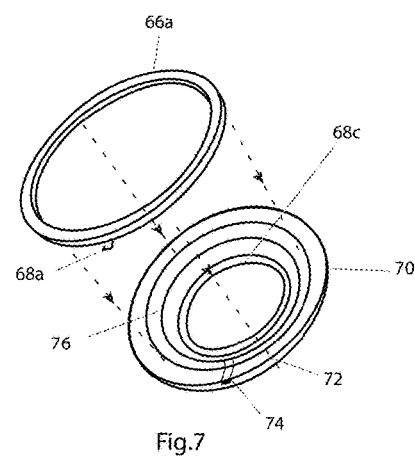

FIG. 7 is an illustration demonstrating the configuration and connectivity of the ring-light, vertex-angulation positioning lights conduction ring and tract, and the light(s) housing segment.

Figure 8:
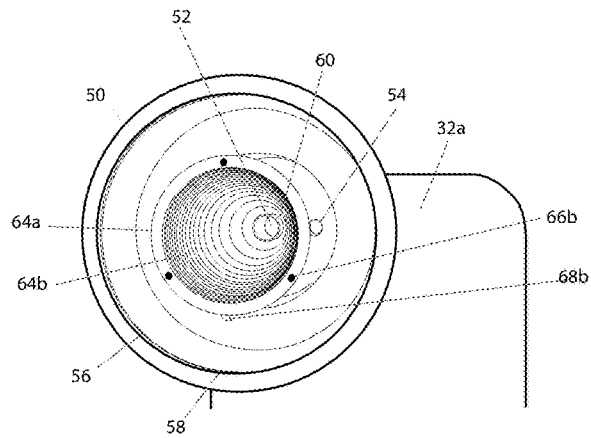

FIG. 8 is a perspective view with ring-light and light housing segment removed illustrating the configuration and connectivity of the optimization lens(es) and/or camera lens(es) tube and the mobile processing device light source aperture/channel of the frustum cone housing segment.

Figure 9:
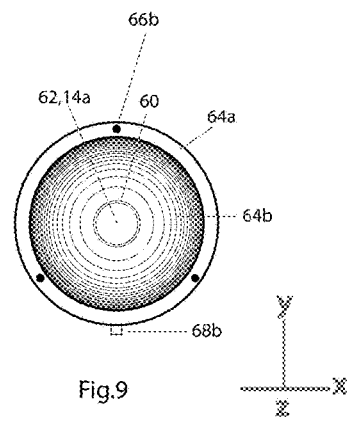

FIG. 9 is a subject perspective view of the frustum cone segment and vertex-angulation positioning light(s) along the z-axis/optical axis.

FIGS. 10-A and 11-A are perspective views of housed illustrations of the system.

FIGS. 10-B and 11-B illustrate the configuration of the ring and vertex-angulation positioning light(s), and the vertex-angulation positioning lights conduction ring and tract to the light(s) housing segment and their connectivity with the light wire conduit from the circuitry within the circuitry housing segment, as well as the ring-light and vertex-angulation positioning light(s) illumination light rays about, and in front of the frustum cone segment, respectively.

FIGS. 12-A and 12-B are perspective views demonstrating ray tracing of some projected concentric rings onto a reference sphere/calibration ball and a cross-sectioned subject patient cornea and/or tear-film layer(s) imaging a target source and subject patient's eye, respectively, as it is used.

FIG. 13-A is an actual image of a reference sphere of +42.50 dioptric (7.94 mm base curve radius) power by a mobile processing device of the Placido disk reflection from the mobile processing device adapted ophthalmological instrument system of FIG. 1.

FIG. 13-B is an actual image of a subject patient cornea and/or tear-film layer(s) by a mobile processing device of the Placido disk reflection from the mobile processing device adapted ophthalmological instrument system of FIG. 1.

FIG. 13-C is a corneal topographic map.

Figure 14:
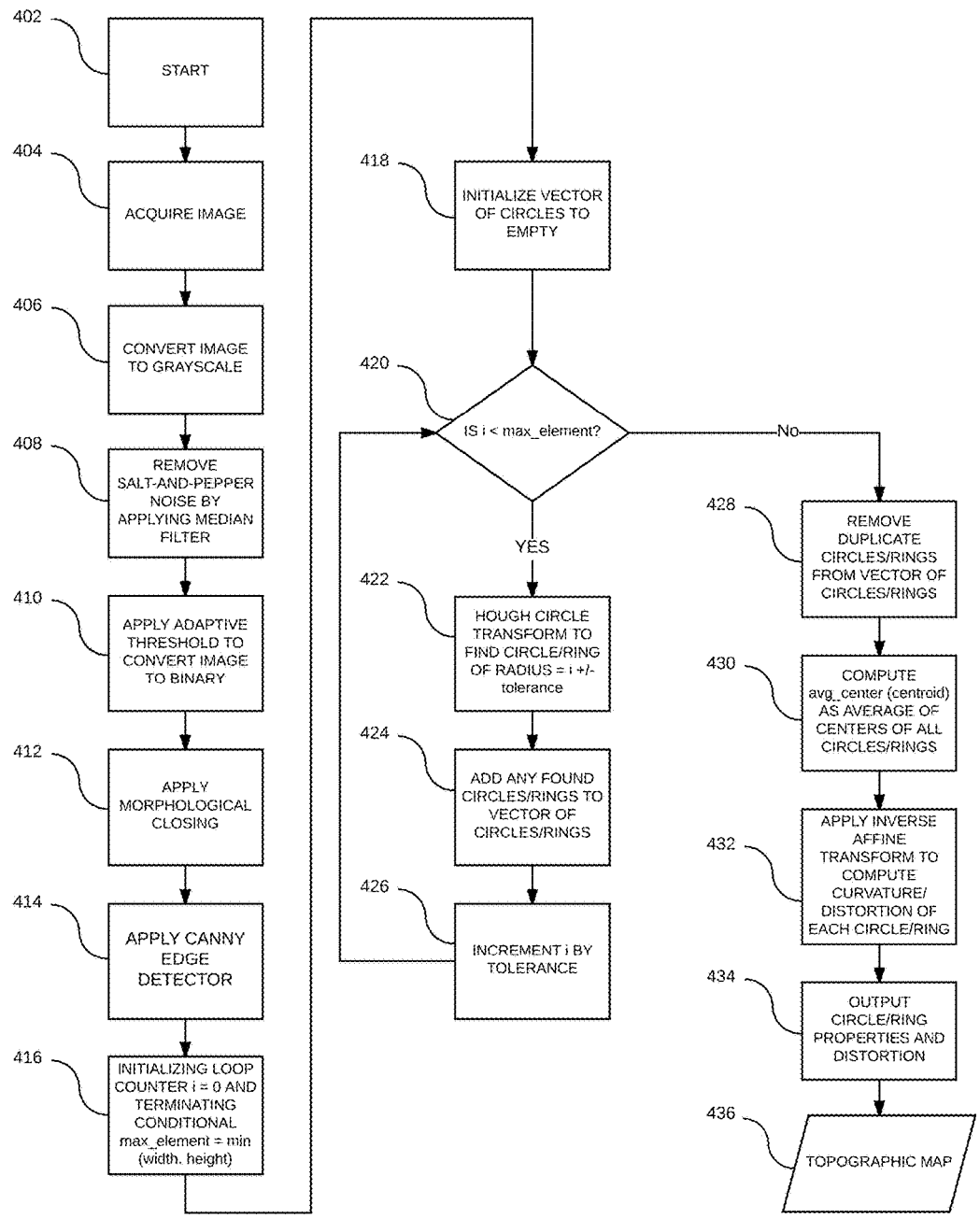

FIG. 14 is a flow chart illustrating the functional operation of the mobile processing device adapted ophthalmological instrument system of FIG. 1 as it implements a process whereby an image of a cornea, tear-film layer(s), and/or target source is captured and the data is subsequently verified and then analyzed to obtain a topographic map.

Figure 15:
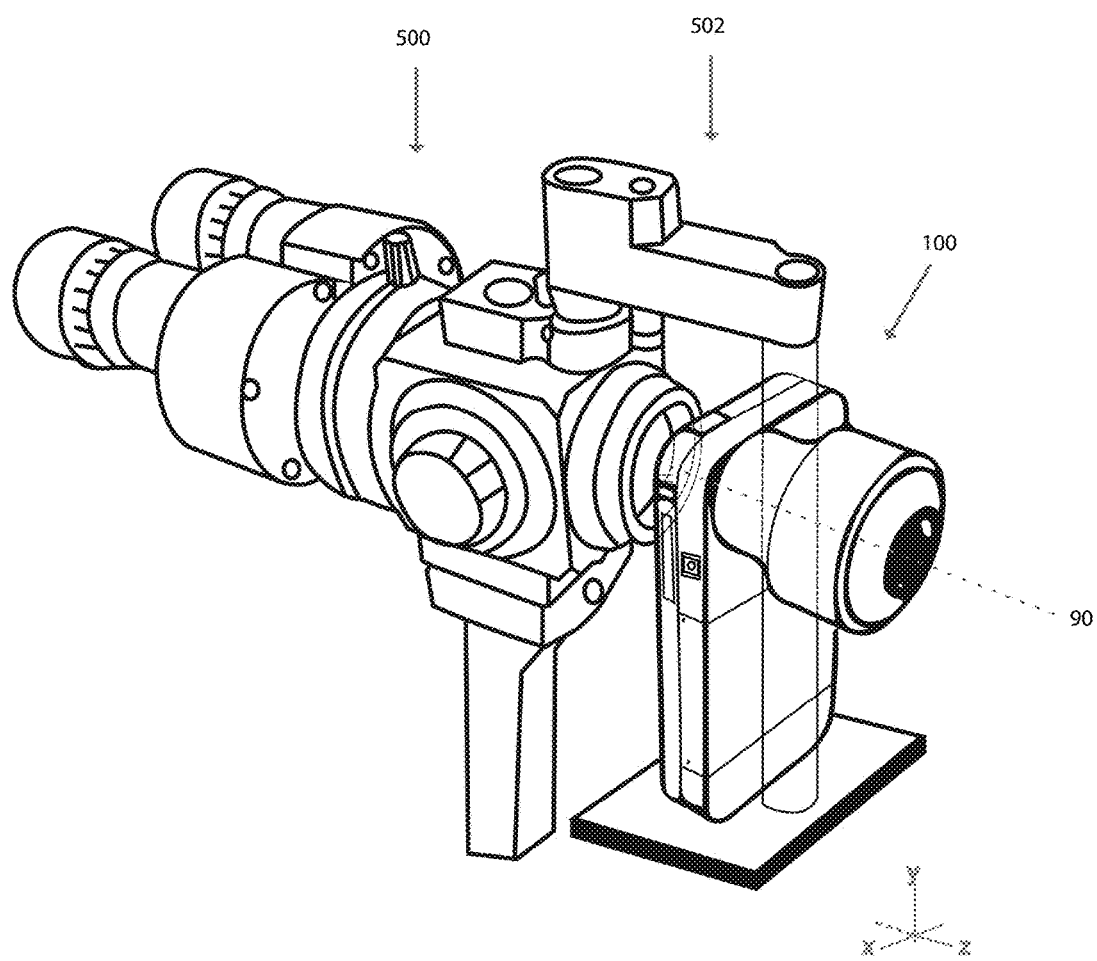

FIG. 15 is an illustration of the system of FIG. 1 adapted to a slit-lamp biomicroscope as it is preferably used and is an additional embodiment of the mobile processing device adapted ophthalmological instrument system.

Figure 16:
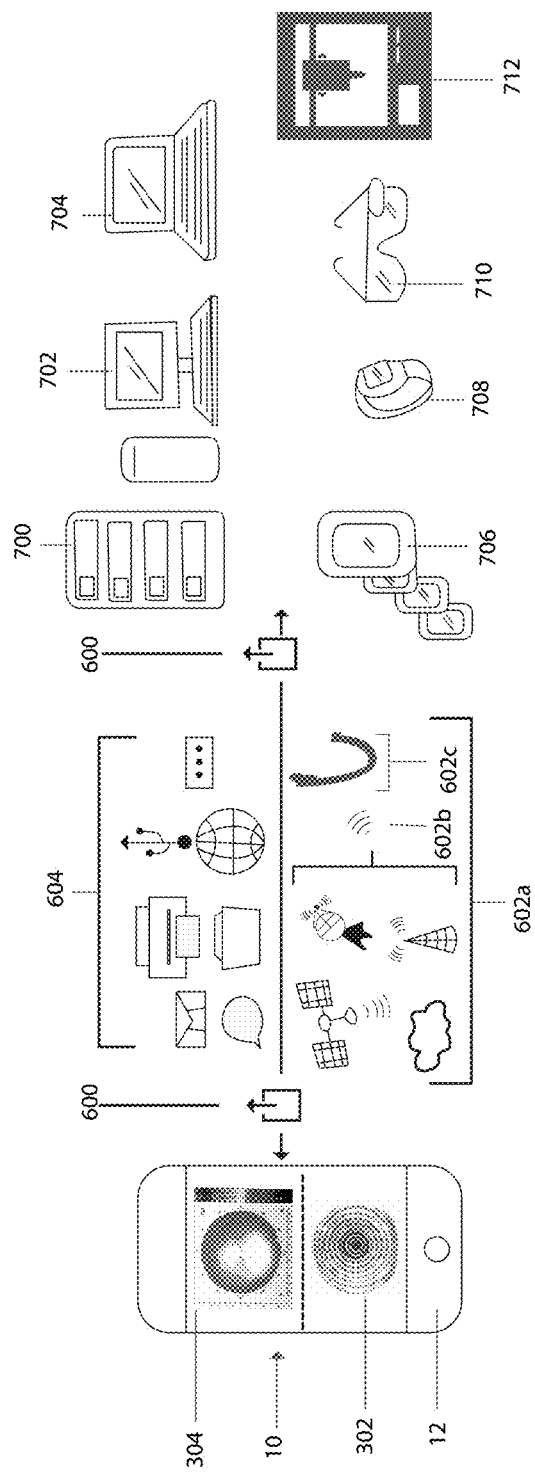

FIG. 16 is an illustration of the communications network transmission potential of the data captured, received, and/or delivered by the mobile processing device and/or dedicated server system via the system in FIG. 1.

V. DETAILED DESCRIPTION OF THE PREFERRED EMBODIMENTS

Described herein is a mobile processing device adapted ophthalmological instrument system 100 which removably attaches to a mobile processing device 10 that operates as an image capture communications device, and preferably a smart-phone 12, in an aligned relationship along the optical axis 90 of the camera lens 14a and the cornea 204 of the test eye 202 of the subject patient 200 and/or target source 203, 204. In the particular embodiment described herein, the mobile processing device that operates as an image capture communications device 10 is a smart-phone 12. The mobile processing device adapted ophthalmological instrument system 100 in-use with a mobile processing device 10, allows the operator to capture, record, save, analyze, and/or transmit images of the cornea 204 and anterior segment of the eye 202. Accordingly, it will be appreciated that the operators of the present invention can be a range of scientists/researchers and/or a range of medical practitioners, such as optometrists, ophthalmologists, other medical or osteopathic physicians, nurses, technicians, residents, students, and caregivers, as well as layperson(s), such as guardians and/or subject patients.

Figure 2:
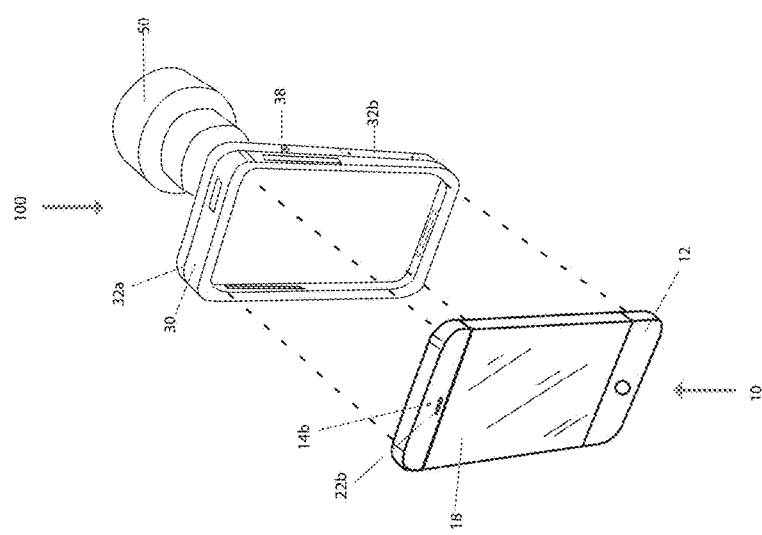
FIG. 2 is a second perspective view of the mobile processing device adapted ophthalmological instrument system of FIG. 1 illustrating the insertion position/connectivity of the mobile processing device.

As shown in FIG. 2, a mobile processing device adapted ophthalmological instrument system 100 removably connects to a smart-phone 12, or within the spirit and scope of the invention, any mobile processing device 10, at the mobile processing device housing segment 30. As illustrated in FIGS. 1-3, the mobile processing device adapted ophthalmological instrument system 100 comprises a mobile processing device housing segment 30, a circuitry housing segment 32a, a battery cover 32b, a frustum cone segment 64a, frustum cone housing segment 50, a light housing segment 70, and an ON/OFF power button 38. The frustum cone segment 64a comprises reference lines wherein a plurality of concentric, circular, frusto-conical, alternating transparent and opaque, illuminated, segment 64a are provided in the conical surface in optical alignment 90 with the mobile processing device's camera lens 14a and subject's 200 central cornea and/or tear-film layer(s) and/or target source 203, 204 in a fashion illustrated in FIG. 3 as it is used. Embedded on and/or within the mouth-end/distal-end walls of the frustum cone segment 64a are vertex-angulation positioning light(s) 66b, specifically, infrared light emitting diodes (IRLEDs) and a vertex-angulation positioning light(s) conduction lead 68b. Spaced-apart/exploded examples in FIGS. 4 and 5, illustrate the components of the mobile processing device adapted ophthalmologic instrument system 100, wherein the system comprises a mobile processing device housing segment 30, a circuitry housing segment 32a, a battery cover 32b, and a mobile processing device camera lens(es) aperture 34 and light source(s) aperture 36. The frustum cone housing segment 50 comprises a frustum cone housing segment-mobile processing device camera lens aperture/channel 52, a frustum cone housing segment-mobile processing device light source aperture/channel 54, a frustum cone housing segment-light housing segment screw-fit grove 56, a light(s) wire conduit 48, and a frustum cone housing segment conduction lead 58. Irremovably nestled within the frustum cone housing segment 50 and in optical alignment with the optical axis 90 of the mobile processing device camera lens 14a and central cornea and/or tear-film layer(s) and/or target source 203, 204, is an optimization lens(es) and/or camera lens(es) tube 60 and a frustum cone segment 64a comprising Placido's rings 64b and vertex-angulation positioning light(s) 66b. Circumscribed about the distal/mouth-end of the frustum cone segment 64a is a ring-light(s) 66a with ring-light leads 68a housed within the light(s) housing segment 70 in a screw-fit manner at the light housing segment-frustum cone housing segment screw-fit groves 72 mating with the screw-fit groves 56 of the frustum cone housing segment. The assembled segments are best illustrated in FIG. 5, wherein the circuitry within the circuitry housing segment 32a and under the battery cover 32b, comprises a power source/battery(ies) 40, a power diffuser/resistor(s) 42, a light(s) wire conduit and/or tracts 48, an ON/OFF power button conduit and/or tracts 46, and a mobile processing device ophthalmological instrument system charging port 44. All assembled segments are configured in orientation wherein their connectivity is aligned along the optical axis 90 to allow for an unobstructed path from the mobile processing device camera lens 14a and the central cornea and/or tear-film layer(s) and/or target source 203, 204.

The mobile processing device could be any image capture communications device that has a camera system. Non-limiting examples of such mobile processing devices include: Brand-independent or operating-system-independent smart-phones, Apple's iPhone® or the iOS operating system, Google's™ Android™ devices and operating system, Blackberry® Windows Mobile®, and other mobile communications and/or image capture devices, such as tablet, laptop, or desktop computers, personal digital assistants (PDAs), MP3 players, iPads, iPods, digital cameras and camcorders, smart-watches, and smart-glasses. The preferred embodiment is via a smart-phone and it will be appreciated that the assembly of the present invention can be applied to and used with any viewing instrument and any image capture, processing, and/or communications device. It will also be appreciated that some and/or all components of the assembly can be designed and/or manufactured, additively and/or subtractively, entirely and/or separately and then be connected removably and/or irremovably, through means known to one skilled in the art. This includes, but is not limited to, those skilled in welding, glue, epoxy, polishing, fabrication, machining, molding, lathing, milling, rapid prototyping, and/or two-dimensional and/or three-dimensional and/or modular designing, modeling, and/or printing, and/or solid free-form fabrication. The assembly can be made of plastic(s) and/of any methacrylate resin(s) and/or acrylics, resins, rubber, metals, alloys, glass, Styrofoam, wood, and/or any combination thereof.

Each one of the means for removably attaching or otherwise connecting or securing the mobile processing device adapted ophthalmological instrument system 100 to any mobile processing device 10, and/or the irremovably connected segments, and/or to the removable light(s) housing segment 70 and ring-light(s) 66a, and/or the removable light(s) housing segment 70 and the frustum cone housing segment 50, and/or, in the preferred embodiment of the present invention, the mobile processing device adapted ophthalmological instrument system 100 to a smart-phone 12, may be any means known to one skilled in the art. Such connections include but are not limited to, a ring-lock clamp, a twist-lock mount, a twist-fit, a snap-fit mount, a screw-fit, a screw mount, a bayonet mount, a friction-fit attachment, sliding slots or grooves, slotted tabs, hook and loop fasteners, magnetism, adhesively-joined attachments, aperture coupling, c-mounting and/or t-mounting, annular rings with set screws, other forms of clamps, and any other method for connecting or securing the segments. As illustrated in FIGS. 6 and 7, the connection between the light(s) housing segment 70 and the frustum cone housing segment 50 is an example of a screw-fit/twist-fit attachment, while the connection between the ring-light(s) 66a and the light(s) housing segment 70 is a snap-fit and/or friction-fit. The connection between the mobile processing device 10 and the mobile processing device housing segment 30 is an example of a snap-fit and/or friction-fit. The removable connection between the circuitry housing segment 32a and the battery cover 32b is an example of a slide-fit and/or screw mount attachment. An exemplary embodiment of the preferred embodiment of the present invention of a mobile processing device adapted ophthalmological instrument system 100 is use with a slit-lamp biomicroscope 500, preferably with a slit-lamp biomicroscope accessory mounting pin and stage 502, and is an example of snap-fit and/or screw mounting, FIG. 15.

In general, the present invention provides a novel method of corneal topography by the invention of a mobile processing device adapted ophthalmological instrument system 100 that connects to a mobile processing device 10 so that the optical axis 90 of the camera lens 14a of the mobile processing device 10 is aligned along the central axis of the frustum cone segment 64a in a secure manner. As particularly shown in FIGS. 2-5, the mobile processing device housing segment 30 houses a smart-phone 12 in a set position in the x, y, and z axes of the mobile processing device adapted ophthalmological instrument system 100. At multiple connections along location 14a of the smart-phone 12 and at different corresponding locations, including the mobile processing device housing segment camera lens aperture 34, the frustum cone housing segment camera lens aperture/channel 52, the optimization lens(es) and/or camera lens(es) tube 60, the frustum cone segment 64a, and the ring-light(s) 66a and light(s) housing segment 70 apertures, segments are secured and aligned in the z-axis along the systems optical axis 90.

The mobile processing device housing segment 30 and/or circuitry/circuitry housing segment 32a can be any case, frame, sleeve, clip, or any of the smart-phone 12 or mobile processing device 10 adapted and/or battery-housed cases, that can be sized or adjusted to fit and/or power any fraction of a mobile processing device 10, and be adapted in modular design to the mobile processing device adapted ophthalmological instrument system 100. Additionally, the mobile processing device 10 can be any mobile communications and/or computing device. Non-limiting examples of adaptable ophthalmological instrument system mobile processing devices include analog and digital cameras, desktop and laptop computers, tablets, MP3 players, PDAs, iPods, iPads, smart-phones, smart-watches, and smart-glasses. More still, larger displays may be more favorable for certain users and/or circumstances, and the orientation of the mobile processing device may be vertical, horizontal, and/or in any two-dimensional and/or three-dimensional degree. Such modifications to size and orientation are a matter of choice and should be appreciated that indications of any mobile processing device is an exemplary description and is not limiting to the scope of this invention. Moreover, the mobile processing device circuitry system power source can be comprised of any battery type(s) or of any combination of battery types. Broadly, the batteries and/or rechargeable batteries can be of a chemical and/or a physical nature. A non-exhaustive list of chemical forms include flow, fuel, lead-acid, lithium air, Li-ion, Mg-ion, molten salt, and/or Ni—Cd. A non-exhaustive list of physical forms includes solar cells and nuclear batteries. Furthermore, is that the power supply system/circuitry can be housed within the frustum cone housing segment. Again, such modifications and size preferences are a matter of choice and should be appreciated that indications of any power supply is an exemplary description and is not limiting to the scope of this invention. What's more, various methods and various stimulator designs and sources can be used to construct corneal topographs, and/or to collect and evaluate additional ocular characteristics. Examples of such stimulator sources are sources that provide a checkerboard or dartboard pattern, and lined or spotted grid assembly patterns. Even more, the light source(s) can be of any shape, orientation, location, and/or composition. Non-limiting examples include light emitting diodes (LEDs), infra-red LEDs, halogen, incandescent, fluorescent, fiber optic, and/or natural room lighting and/or natural sources (i.e. sun). The light sources may also be of any color(s), be commanded to change intensity, flicker, and/or color, and/or be clear, coated, or frosted, and/or emanate from the mobile processing device and/or a separate light source(s) within or about the mobile processing device adapted ophthalmological instrument system. The optimization lens(es) can also be modified by preference with various coatings, powers, shapes, sizes, positions, filters, polarizations, prisms, mirrors, and/or with adaptive optics. Non-limiting, exemplary embodiments of the present invention include (i) the utility of ocular surface tear quality characterization and analysis, which is carried out by observing and/or analyzing reflected stimulator source patterns, (ii) determining from additionally reflected ring projections from the posterior corneal surface, the posterior corneal surface curvature, (iii) determining all local shape variations on and between the anterior corneal surface and the posterior corneal surface, and (iv) determining the thickness of the cornea. Tear quality characterization and analysis testing can be through image capture after sustained episodes of non-blinking and/or at any moment and in any capacity during and between eye blinking, and/or imaging and/or analyzing the tear-film layer(s) before and after treatment(s), and/or imaging and/or analyzing tear-film birefringence pattern(s). Other methods of constructing topographs are by establishing additional fixation points to create multiple viewing axes. Also, alternate illumination technologies can be used to enhance the contrast and resolution of the reflected patterns. Although the present invention described herein and hereinafter is in detail with reference to a particular preferred embodiment, persons possessing ordinary skill in the art to which this invention pertains will appreciate that various modifications and/or enhancements may be made without departing from the spirit and scope of the claims written and as judicially construed according to principles of the law. Therefore, and as earlier mentioned, it should be understood that the detailed descriptions, specific examples, and drawings, while indicating the preferred embodiment of the invention, are intended for purposes of illustration only and are not intended to limit the scope of the invention.

As particularly shown in FIGS. 3, 11-B, and 12-B, and in the preferred embodiment of this invention, a subject patient's head 200 is located to position an eye 202 to be observed through the unobstructed smart-phone display screen 18 with the cornea and/or tear-film layer(s) 204 of the eye vertexed, angulated, and centered along the system's optical axis 90. Furthermore, as illustrated in FIG. 9, the frustum cone segment's fixation point 62 is aligned with the optical axis of the system 90 and may or may not be illuminated as a distinct center ring and/or spot at the base/hole of the frustum cone segment 64a of the mobile processing device adapted ophthalmological instrument system 100. FIG. 11-B is a cross-sectional view of the frustum cone segment 64a with the frustum cone housing segment outlined to maintain a boundary wherein ray-tracing 130 of the housed and reflected illumination projections of the ring-light(s) 66a about the frustum cone segment 64a is illustrated. FIGS. 12-A and 12-B are cross-sectional views of the frustum cone segment 64a demonstrating ray-tracings 150 of some of the frustum cone segment concentric segment 64a being projected onto a target source, and/or cornea, and/or tear-film layer(s) 203, 204, respectively. FIGS. 3, 13-A, and 13-B show the imaging 300, 302 embodiment of the present invention as it is used in operation with one of a plurality of reference/calibration spheres 203 and/or subject patient 200 cornea and/or tear-film 204. FIGS. 3-5, 10-12, and 15 show the entire assembly of the mobile processing device adapted ophthalmological instrument system 100 to be in optical alignment. Furthermore, the entire assembly of the mobile processing device adapted ophthalmological instrument system 100 with attached mobile processing device 10, provides for a firm and stable assembly at a well-functioning angle for examining a subject patient's eye.

Illustrated in FIGS. 4-9, 10-B and 11-B, the mobile processing device adapted ophthalmological instrument system 100 comprises a feature to address vertex and angulation positioning by a triangulation of vertex-angulation positioning light(s), in particular, infrared light emitting diodes (IRLEDs) 66b situated equidistantly at the mouth/distal-end of the frustum cone segment 64a, communicating with the light(s) housing segment 70 via the vertex-angulation positioning lights conduction ring and tract 68c, and configured to focus light rays 140 toward the frustum cone center along the z-axis, FIG. 11-B, 1-mm in front of the mouth/distal-end of the frustum cone segment 64a along the system's optical axis 90. As a target source 203, 204 is situated to the mobile processing device adapted ophthalmological instrument system 100 frustum cone segment 64a, crossed or uncrossed, intercepted infrared light rays 140 form a plurality of observable focal points on the target source, observed by the camera lens 14a of the mobile processing device 10 and displayed on the mobile processing device's display screen 18. Only when the target source 203, 204 reaches the appropriate vertex distance (1 mm) from the center of the mouth/distal-end of the frustum cone segment 64a, will the operator observe an absence of a plurality of IRLED focal points, in other words, singularity. With singularity, the mobile processing device's display screen 18 will show a centered, monofocal-point 306 wherein each IRLED light ray 140 has converged, FIGS. 13-A and 13-B. Modifications to the vertex-angulation positioning light(s) and/or type(s), such as varying absorption, transmission, and/or emission spectra, color, size, positioning, and/or orientation is a matter of choice and it should be appreciated that indications of any positioning light(s) is an exemplary description and is not limiting to the scope of this invention. Moreover, vertex distance could be generally addressed with an understanding of horizontal visible iris diameter (HVID) normative data. A series of independent studies comprised of 200 and 100 consecutive eyes determined an average HVID of 11.8 mm. Additionally, both studies found that 9% and 13.5% of patients had a HVID of 11.3 mm or smaller and that 13% and 8% of patients had a HVID of 12.3 mm or larger. Given this data, setting a peripheral limit on a peripheral ring(s) within the frustum cone segment 64a would roughly capture the majority of target sources 203, 204 at an ideal vertex distance. Even more accurately, is determining the HVID of each target source 203, 204 and imagining the horizontal visible iris diameter limits coincident with ring(s) limits set for such HVID at a set vertex distance (i.e. 1 mm). These methods of vertex distance determination is matter of choice and is an exemplary description not limiting the scope of this invention.

The present invention can be used directly and/or remotely, manually and/or automatically, or as in an exemplary embodiment, be attach to a number of medical devices, i.e. slit-lamp biomicroscope 500, as preferably shown in FIG. 15, and be used as an attachable (stationary) and/or detachable (portable) mobile processing device adapted ophthalmological instrument system 100. The mobile processing device adapted ophthalmological instrument system 100 can connected to the slit-lamp biomicroscope 500 in a fashion onset and/or offset from the optical axis of the slit-lamp biomicroscope by a slit-lamp biomicroscope accessory mounting pin and stage 502.

In the preferred embodiment of the present invention, software applications downloaded to and/or accessed by the smart-phone's processor(s) 20 analyze captured, received, and/or delivered images 300, 302 of a subject's cornea, and/or tear film layer(s), and/or target source 204, 203 and compare and/or determine data of shape, structure, composition, function, and/or power of the subject cornea(s), and/or tear-film layer(s), and/or target source(s) 204, 203 by methods comprising one or more software algorithms and/or operators configured to receive and/or process captured and/or real-time images from and/or to a mobile processing device's camera lens(es) and/or media storage system(s), wherein the algorithm(s) and/or operator(s) comprise one or more image processing and/or computer vision functions including but not limited to segmentation, enhancement, association, decomposition, inversions and/or conversions, thresholding, normalization, sampling, thinning, dilation-erosion (closing) and/or erosion-dilation (opening) morphology(ies); centroid(s), segment(s), length(s), width(s), height(s), radii, diameter(s), area(s), circumference(s), and/or volume(s) detection and/or identification and/or determination; photogrammetry; Affine, Fourier, Hough, generalized Hough, Cao-Deravi, Ioannou, Top-Hat, Pixel, Color, Distance, Canny and/or Deriche transformations and/or primitives and/or invariances; Zernicke polynomials and/or Gaussian operator(s); templates and/or deformable templates; shape, reflectance, shading, contour, edge, direction, color, intensity, texture, contrast and/or motion detection(s); image-based rendering and/or modeling; point spread functions (PSF); RANdom SAmple Consensus (RANSAC); projections, filtering, patching, linking, thresholding, arc-step, arc-length, parameterization, tracking; stereo and/or space-time stereo correspondence processes; reconstruction, modeling, point-based representation(s), recognition, context and scene understanding, pixelation, and/or feature extraction and matching methods, to produce qualitative and/or quantitative information and/or a two-dimensional and/or three-dimensional topographic map(s) 304 and/or printings and/or a histogram(s) from Placido's disk reflected images 300, 302 of a target source(s) and/or cornea(s) and/or tear-film layer(s) 203, 204. FIG. 14 is a flow chart 400 generally illustrating the functional operation of the mobile processing device adapted ophthalmological instrument system of FIG. 1 as it implements a process whereby an image of a cornea, tear-film layer(s), and/or target source is captured/acquired 404 and converted into grayscale 406. The image is then filtered for salt-and-pepper noise reduction by applying a median filter of size 7×7 pixels 408 and adaptive thresholding to convert the image to a binary image 410. Subsequent morphological closing and/or opening with 5×5 pixel structuring elements are applied (all 1's) 412. Following Canny edge detection for circle/ring identification 414, a loop counter (i) algorithm is initialized wherein loop counter, i=0 and terminating conditional max_element=min (width, height) of input image 416. Next, a process to initialize vector of detected circles/rings to empty 418 is followed by selectively 420 utilizing the Hough circle transform 422 if the loop counter (i) is less than max_element 420. The Hough circle 422 finds circles/rings of radius equal to the loop counter (i) +/− tolerance and adds any found circle(s)/ring(s) to the vector of circles/rings 424. Next, the process increments loop counter (i) by tolerance 426 repeatedly, until the loop counter criteria of i<max_element is not met. When the loop counter criteria of i<max_element is not met, a process which removes duplicate circles/rings from vector of circles/rings 428 is carried out, followed by computing an average center (centroid) as an average center of all circles/rings 430. The inverse affine transform is applied to compute curvature(s) and/or distortion(s) of each circle/ring 432, whereby an output 434 of all the imaged circle/ring properties are translated into a topographic map/data 436 of the captured, received, and/or delivered image(s).

In one embodiment, the mobile processing device can take, store, and/or transmit still images (photographs). In another embodiment, the same device may record, store, and/or transmit motion images (videos). In yet another embodiment, the same device is capable of taking, storing, and/or transmitting photographs and videos, again, collectively referred as images. In a further embodiment, the image(s) may be used to print two and/or three-dimensional spectacles and/or contact lenses and/or eye-models. In yet a further embodiment, the same device may record, store, and/or transmit audio along with images. The image and/or audio records may be viewed and analyzed either on the same device or on other systems, as described below.

While the present invention is particularly described with reference to the mobile processing device adapted ophthalmological instrument system 100 as it attaches to a smart-phone 12, it will be appreciated that the smart-phone 12 could also be used to connect to other computer systems that may or may not have image capture capabilities. As shown in FIG. 16, the present invention takes advantage of the smart-phone's computer processor 20, which allows the user to communicate 600 captured images, audio, and any information over a communications network 602a through a wireless 602b and/or wired 602c transmission. The captured images 300, 302, constructed and/or received topographies 304, and/or any information, may be stored, printed, saved, and/or shared 604 with a centralized server(s) 700, desktop computer(s) 702, laptop computer(s) 704, other smart-phones, iPads, iPods, and/or tablets 706, smart-watches 708, smart-glasses 710, and/or 3D-printers 712. The information can also be retransmitted across the communications network 602a back to the smart-phone 12. Once received, the captured images 300, 302, corneal topographies 304, and other information, can be communicated from, and between, the receiving systems. The smart-phone's computer processor 20 can also run applications that can be used for taking examination records or notes, annotating, processing, and storing the captured images. More still, the smart-phone's computer processor 20 and image/video enhancement effects applications 250 can help optimize the quality of the captured images 300, 302 obtained from testing, such as shown in FIG. 3, or constructed or received corneal topographies 304, as shown in FIG. 13-C. The smart-phone can perform other image processing functions such as autofocusing adjustments to optimize the live subject views, allow for image magnification/zoom of either live subject views or captured images, be commanded to directly and/or remotely, manually and/or automatically, capture images and/or multiple images in series over several seconds, or be adjusted to either increase or decrease the illumination intensity, duration, and auto-shutter or flash 252 of the mobile processing device light source 16 illuminating the frustum cone segment 64a within the frustum cone housing segment 50. The microphone 24, headphone jack 26, and speakers 22a, 22b of the smart-phone 12 can also be used for taking and listening to voice notes, which may include capturing, storing, and replaying audio recordings with video recordings of the subject patient 200.

The present invention allows a user to capture images 302 of a patient's eye 202 in-office and in out-of-office settings, and to construct corneal topographs 304 in real-time or post hoc. Out-of-office settings might be when it is impractical or impossible to bring traditional equipment capable of imaging the eye. Out-of-office settings include, but are not limited to, mission trips, community outreach health fairs and health screenings, medical volunteerships, and outreach programs. In the preferred embodiment of the present invention, the smart-phone's computer processor 20 allows the user to communicate with physically present and/or absent medical eye specialists, such as ophthalmologists and optometrists, who may help with the evaluation, diagnosis, and treatment of the patient subject eye(s); in other words, telemedicine. In an alternate embodiment, the images, and/or other information, may be transmitted and/or transferred from the mobile processing device 10 to a computer system of a network of physicians, researchers/scientists, medical and/or optometric residents, or medical and/or optometric students. In a further embodiment, the information can include patient data and patient medical history to aid medical and/or research personnel in analysis of the images.

It will be appreciated that the present invention of a system and method for ophthalmological imaging adapted to a mobile processing device, in the preferred embodiment, provides eye and non-eye specialists a method of obtaining corneal, tear-film layer(s), and/or target source topographies at a much lower cost than the more traditional corneal topography technology. It will also be appreciated that one of ordinary skill in the art to which this invention pertains acknowledges that alternate but functionally equivalent components, materials, designs, and equipment may be used, particularly other image capture, receiving, and/or delivering devices. Specific elements disclosed herein are not to be interpreted as limiting. Rather, the specific elements disclosed serve as a basis for the claims and as a representative basis for teaching one of ordinary skill in the art to employ the present invention. Additionally, the terms "substantially", "approximately" and/or "sustained" as used herein may be applied to modify any quantitative representation that could permissibly vary without resulting in a change to the basic function to which it is related. Furthermore, the use of definite and/or indefinite articles, especially in the context of the following claims, and similarly used referents, are to be understood to cover the singular and the plural, unless otherwise noted. The use of the terms "comprise(s)", "comprising", "has", "have", "include(s)", "including", and "consist(s)" are to be construed as open-ended terms that means the purpose is "not limited to". The terms used to describe the connectivity of the segments, units, and/or system is to be construed as meaning in any capacity, whether partly and/or wholly, within and/or about, removably and/or irremovably, unless otherwise noted. Accordingly, the above description is intended to cover such alternatives, modifications, and equivalents as may be included within the spirit and scope of the invention as defined by the appended claims. The above disclosure is thus intended for purposes of illustration and not limitation.

What is claimed is:

1. An ophthalmological instrument system configured to a mobile processing device having an imaging system comprising at least one from the group comprising a computer processor(s), and a communications module(s), comprising:

a mobile processing device housing segment removably attached to a mobile processing device, and removably or irremovably attached to a frustum cone housing segment, wherein said mobile processing device housing segment comprises apertures coincident and/or coaxial with the mobile processing device's camera lens(es) and light source(s);

a frustum cone segment securely connected within said frustum cone housing segment in a fixed position in optical alignment with said mobile processing device's camera lens(es) and at least one from the group comprising subject's central cornea, tear-film layer(s), and target source(s), whereby said frustum cone segment comprising a pattern(s) is configured to project an illuminated said pattern(s) onto at least one from said group comprising, cornea, tear-film layer(s), and target source(s) disposed on the mouth-end/distal-end of said frustum cone segment; and a light(s) housing segment removably secured to said frustum cone housing segment, wherein a homogenously illuminating ring-light(s) is removably fitted to evenly illuminate said frustum cone segment whereby said frustum cone housing segment provides a controlled light environment within said frustum cone housing segment and about said frustum cone segment, enabling said mobile processing device's camera lens(es) to image reflections of said illumination pattern(s) from at least one from said group comprising, said cornea, said tear-film layer(s), and said target source(s); and automatically and/or manually generating from said image(s) output of at least one from the group, comprising, shape, structure, thickness, composition, function, power, and topographic map(s) of the data.

2. The system of claim 1, wherein said frustum cone housing segment further comprises mobile processing device camera lens(es) and light source(s) apertures, whereby said mobile processing device's light source(s) project into said frustum cone housing segment, operatively cooperating to illuminating said frustum cone segment.

3. The system of claim 1, further comprising an optimization lens(es) and/or camera lens(es) tube within said frustum cone segment, adjacent to, circumscribing, and in optical alignment with said mobile processing device's camera lens(es) and said subject's central cornea, tear-film layer(s), and/or target source(s), whereby said optimization lens(es) and/or camera lens(es) tube blocks back-scattered light from being incident onto said mobile processing device's camera lens(es) and/or optimization lens(es) by said mobile processing device's light source(s) and/or from said ring-light(s).

4. The system of claim 3, wherein said optimization lens(es) housed within said lens tube, comprise anti-reflective coating(s) whereby reducing light back-scatter incident upon and/or about said mobile processing device's camera lens(es).

5. The system of claim 1, wherein said frustum cone segment further comprises reference lines wherein a plurality of concentric, circular, frusto-conical, alternating transparent and opaque, illuminated, rings (Placido's disk) and/or pattern(s) are provided in the conical surface in optical alignment with said mobile processing device's camera lens(es) and said subject's central cornea, and/or tear-film layer(s), and/or target source(s), wherein said reference lines characterize geometrical requirements whereby reflected rings upon a reference sphere of base curve radius corresponding to the normal curvature of the surface to be analyzed, are equidistant with respect to one another.

6. The system of claim 1, wherein said frustum cone segment further comprises vertex-angulation positioning light(s) therein, and a vertex-angulation positioning light(s) conduction lead thereon said frustum cone segment, wherein said vertex-angulation positioning light(s) project a plurality of beams triangulated outward from said frustum cone segment in a direction of said subject's central cornea, tear-film layer(s), and/or target source(s), along said optical axis whereby positioning said subject's central cornea, tear-film layer(s), and/or target source(s) at the proper vertex distance produces a singularity of beam focal points.

7. The system of claim 6, whereby said vertex-angulation positioning light(s) and lead of said frustum cone segment are removably secured in connectivity with the vertex-angulation positioning light(s) conduction ring and tract on said light(s) housing segment, whereby the light(s) housing segment conduction lead links said vertex-angulation positioning light(s) and said ring-light(s) to the frustum cone housing segment conduction lead, where then the light(s) wire conduit relays to the circuitry housing segment.

8. The system of claim 7, whereby said light(s) housing segment removably secures to said frustum cone housing segment at respective screw-fit and/or twist-fit groves, wherein said ring-light(s) further comprise a ring-light(s) lead, removably secured in connectivity to said light(s) housing segment conduction lead.

9. The system of claim 7, wherein said circuitry housing segment further comprises battery(ies), a power diffuser/resistor(s), circuit conduits/tracts, a battery cover, a charging port, and a controllable ON/OFF system power button.

10. The system of claim 1, further comprising one or more processors configured with executable functions and/or algorithms to analyze said Placido's disk-reflected image(s) and/or pattern(s) captured, received, and/or delivered by said mobile processing device's camera lens(es) and/or said processors of said images of said subject's cornea(s), tear-film layer(s), and/or target source(s), and to generate a topographic map(s) of the data.

11. The system of claim 1, whereby said mobile processing device comprises any image and/or video capture communications device that has a camera system(s), wherein non-limiting examples of such mobile processing devices include: Brand-independent or operating-system-independent smart-phones, Apple's iPhone® or the iOS operating system, Google's™ Android™ devices and operating system, Blackberry® Windows Mobile®, and other mobile communications and/or image capture devices, such as tablet, laptop, or desktop computers, personal digital assistants (PDAs), MP3 players, iPads, iPods, digital cameras and camcorders, smart-watches, and smart-glasses.

12. The system of claim 11, where in the preferred embodiment, said mobile processing device comprises a smart-phone.

13. The method for using an ophthalmological instrument system configured to a mobile processing device having an imaging system comprising at least one from the group comprising a computer processor(s), and a communications module(s), comprising:

securely positioning said mobile processing device into a mobile processing device housing segment of system, wherein the mobile processing device's camera lens(es) is unobstructedly coaxial with the optical axis of at least one from the group comprising subject's central cornea(s), tear-film layer(s), and target source(s);

positioning the mouth-end/distal-end of a housed frustum cone segment comprising at least one of the group comprising a Placido's disk(s), and a pattern(s) adjacent to at least one from said group, comprising said subject's cornea, tear-film layer(s), and target source and directing subject's fixation along system's said optical axis into said mobile processing device's camera lens(es) and/or innermost center ring of said frustum cone segment;

illuminating said frustum cone segment comprising at least one of said group comprising Placido's disk(s), and pattern(s), for an evaluation period by powering ring-light(s) and vertex-angulation positioning light(s), wherein said evaluation period is a greater time than a picture-taking period;

receiving at said mobile processing device's camera lens(es), a reflected image(s) comprising at least one of said group comprising Placido's disk(s), and pattern(s) off of at least one of said group comprising, said subject's cornea(s), said tear-film layer(s), and said target source(s);

displaying on a display screen(s) of said mobile processing device, said reflected Placido's disk(s) and/or pattern(s) image off of at least one of said group, comprising said subject's cornea(s), tear-film layer(s), and target source(s);

moving said ophthalmological instrument system configured to a mobile processing device with removably secured said mobile processing device until said vertex-angulation positioning light(s) triangulating a plurality of focal points display a singularized focal point on said mobile processing device's display screen(s);

capturing said reflected Placido's disk image(s) and/or pattern(s) of at least one of said group, comprising subject's cornea(s), tear-film layer(s), and target source(s) when said vertex-angulation positioning light(s) are singularly focused at pre-selected vertex focal point, directly and/or remotely, manually and/or automatically;

comparing the positioning of a plurality of data points of said reflected Placido's disk image(s) and/or pattern(s) of at least one of said group comprising subject's cornea(s), tear-film layer(s), and target source(s) with data of a plurality of corresponding data points from images of a plurality of reference/calibration spheres;

producing at least one from the group comprising, shape, structure, thickness, composition, function, power, and topographic map(s) of at least one from the group, comprising, subject's cornea(s), tear-film layer(s), and target source(s) based on the results of the comparison; and sharing of said reflected Placido's disk image(s) and/or pattern(s) and/or sharing of at least one from the group comprising, shape, structure, thickness, composition, function, power, and topographic map(s) of at least one from the group comprising subject's cornea(s), tear-film layer(s), and target source(s), and/or additional information, through a communications network to at least one from the group comprising, a network of computer systems, scientists, medical professionals, and students.

14. The method of claim 13, wherein said mobile processing device removably secures to said mobile processing device housing segment, whereby said frustum cone segment, optimization lens(es), and said optimization lens(es) and/or camera lens(es) tube are fixed in optical alignment with said mobile processing device's camera lens(es).

15. The method of claim 13, wherein said light(s) housing segment removably securing a ring-light(s), further comprises a ring-light(s) fitting grove, whereby positioning said ring-light(s) to project circumferentially and homogenously about said frustum cone segment at mouth-end/distal-end toward said frustum cone axial hole within a controlled environment housed by said frustum cone housing segment, and whereby said optimization lens(es) and/or camera lens(es) tube shades said mobile processing device's camera lens(es) and/or said optimization lens(es).

16. The method of claim 13, wherein an alternate embodiment of imaging said subject cornea(s), tear-film layer(s), and/or target source(s) and constructing topographs comprising additional fixation points, creating multiple viewing axes, wherein a plurality of said reflected Placido's disk image(s) and/or pattern(s) can be used to produce and/or determine at least one from said group comprising shape, structure, thickness, composition, function, power and said topographic data.

17. The method of claim 15, wherein the method further comprises passing reflected light from said subject's cornea(s), tear-film layer(s), and/or a target source(s) through said frustum cone, said optimization lens(es) and/or camera lens(es) tube, and/or said optimization lens(es) through said mobile processing device's camera lens(es), wherein said passing reflected light comprises a pattern of reference lines of a plurality of concentric, circular, frusto-conical, alternating transparent and opaque, illuminated, rings (Placido's disk) and/or pattern(s), whereby said reflected Placido's disk and/or pattern(s) from said subject's cornea(s), tear-film layer(s), and/or a target source(s) is unobstructedly displayed on said display screen(s) of said mobile processing device.

18. The method of claim 13, wherein said ophthalmological instrument system configured to a mobile processing device comprises a plurality of cooperative and/or mutually exclusive methods of vertex-angulation positioning.

19. The method of claim 18, wherein said vertex-angulation positioning light(s) singularly focus at a pre-selected vertex focal point of 1 mm from apex of said subject's central cornea, tear-film layer(s), and/or a target source.

20. The method of claim 18, wherein said frustum cone segment further comprises setting a peripheral limit on a peripheral ring(s) of said Placido's disk(s) and/or pattern(s) within said frustum cone segment coincident with a pre-selected vertex distance (i.e. 1 mm).

21. The method of claim 18, whereby determining a horizontal visible iris diameter of said subject's cornea(s), tear-film layer(s), and/or a target source(s) and imaging said horizontal visible iris diameter coincident with pre-set ring positions of said Placido's disk(s) and/or pattern(s) reflections, at a pre-set vertex distance (i.e. 1 mm).

22. The method of claim 13, wherein said mobile processing device comprises image enhancement effects applications, a controllable light-flash option, and camera and/or image zoom features, whereby said mobile processing device comprises any image capture communications device that comprises a camera system(s), wherein non-limiting examples of mobile processing devices include: Brand-independent or operating-system-independent smart-phones, Apple's iPhone® or the iOS operating system, Google's™ Android™ devices and operating system, Blackberry® Windows Mobile®, and other mobile communications and/or image capture devices, such as tablet, laptop, or desktop computers, personal digital assistants (PDAs), MP3 players, iPads, iPods, digital cameras and camcorders, smart-watches, and smart-glasses.

23. The method of claim 22, where in the preferred embodiment, said mobile processing device comprises a smart-phone.

24. The method of claim 13, whereby comparing a plurality of corresponding data points comprises computer vision and/or image processing methods, wherein said methods of computer vision and/or image processing further comprise comparing and/or determining data of shape, state, structure, composition, function, and/or power of said subject cornea(s), and/or tear-film layer(s), and/or target source(s).

25. The method of claim 24, wherein said computer vision and/or image processing comprises one or more software algorithms and/or operators configured to receive and/or process captured and/or real-time images from and/or to said mobile processing device's camera lens(es) and/or media storage system(s).

26. The method of claim 25, wherein said algorithm(s) and/or operator(s) comprise one or more said image processing and/or computer vision functions including but not limited to segmentation, enhancement, association, decomposition, inversions and/or conversions, thresholding, normalization, sampling, thinning, dilation-erosion (closing) and/or erosion-dilation (opening) morphology(ies); centroid(s), segment(s), length(s), width(s), height(s), radii, diameter(s), area(s), circumference(s), and/or volume(s) detection and/or identification and/or determination; photogrammetry; Affine, Fourier, Hough, generalized Hough, Cao-Deravi, Ioannou, Top-Hat, Pixel, Color, Distance, Canny and/or Deriche transformations and/or primitives and/or invariances; Zernicke polynomials and/or Gaussian operator(s); templates and/or deformable templates; shape, reflectance, shading, contour, edge, direction, color, intensity, texture, contrast and/or motion detection(s); image-based rendering and/or modeling; point spread functions (PSF); RANdom SAmple Consensus (RANSAC); projections, filtering, patching, linking, thresholding, arc-step, arc-length, parameterization, tracking; stereo and/or space-time stereo correspondence processes; reconstruction, modeling, point-based representation(s), recognition, context and scene understanding, pixelation, and/or feature extraction and matching methods.

27. The method of claim 26, whereby qualitative and/or quantitative information and/or a two-dimensional and/or three-dimensional said topographic map(s) and/or printings and/or histogram(s) from said Placido's disk reflected image(s) and/or pattern(s) from said subject cornea(s), tear-film layer(s), and/or target source(s) is produced.

28. The method of claim 13, wherein the data further comprises patient medical history, subject biometrics, voice, and/or video records which may aid software, medical and/or research personnel in diagnoses and treatments.

29. The method of claim 13, wherein said mobile processing device processor(s), allows the operator to communicate with present and/or absent medical and/or medical eye specialists, whereby communication of said data to present and/or absent medical and/or medical eye specialists comprises telemedicine.

30. The method of claim 28, wherein a plurality of said data may be saved, stored, transmitted and/or transferred from the mobile processing device to a network of computer systems and/or to a network of physicians, researchers/scientists, medical and/or optometric residents, or medical and/or optometric students, or from said computer systems to said mobile processing device.

31. The method of claim 30, wherein said network of computer systems comprise servers, desktop and laptop computers, tablets and personal digital assistants, ipads and ipods, smart-phones, smart-watches, smart-glasses, and two-dimensional and three-dimensional printers.

32. The method of claim 13, whereby said ophthalmological instrument system configured to said mobile processing device can be removably fitted to a slit-lamp biomicroscope in a secure fashion, preferably by an accessory mounting pin and/or stage system(s), whereby with nestled said mobile processing device in said mobile processing device housing segment, said mobile processing device's camera lens(es) is unobstructedly coaxial with the optical axis of at least one from said group comprising subject's central cornea, tear-film layer(s), and target source(s).

33. The method of claim 32, wherein said slit-lamp biomicroscope accessory mounting pin and/or stage system(s) comprises removably securing said ophthalmological instrument system configured to a mobile processing device mobile processing device in a screw-fit and/or snap-fit fashion, wherein swinging said accessory mounting pin and/or stage system(s) into an activated, testing position, is a secure orientation for testing live subject patients.

34. The method of claim 32, wherein said slit-lamp biomicroscope accessory mounting pin and/or stage system(s) removably secures said ophthalmological instrument system configured to a mobile processing device, to said slit-lamp biomicroscope in a manner, preferentially, onset and/or offset from the optical axis of said slit-lamp biomicroscope and/or slit-lamp biomicroscope imaging systems, wherein said mobile processing device's display screen(s) is unobstructed while in said activated and/or inactivated positions and/or in-use or out-of-use, whereby an out-of-use/non-active position renders the slit-lamp biomicroscope active for conventional slit-lamp biomicroscopic testing.

35. The method of claim 33, wherein said slit-lamp biomicroscope accessory mounting pin and/or stage system(s) removably secures said ophthalmological instrument system configured to a mobile processing device, to said slit-lamp biomicroscope in a manner, preferentially, onset and/or offset from the optical axis of said slit-lamp biomicroscope and/or slit-lamp biomicroscope imaging systems, wherein said mobile processing device's display screen(s) is unobstructed while in said activated and/or inactivated positions and/or in-use or out-of-use, whereby an out-of-use/non-active position renders the slit-lamp biomicroscope active for conventional slit-lamp biomicroscopic testing.

36. The method of claim 14, whereby said ophthalmological instrument system configured to said mobile processing device can be removably fitted to a slit-lamp biomicroscope in a secure fashion, preferably by an accessory mounting pin and/or stage system(s), whereby with nestled said mobile processing device in said mobile processing device housing segment, said mobile processing device's camera lens(es) is unobstructedly coaxial with the optical axis of at least one from said group comprising subject's central cornea, tear-film layer(s), and target source(s).

37. The method of claim 16, whereby said ophthalmological instrument system configured to said mobile processing device can be removably fitted to a slit-lamp biomicroscope in a secure fashion, preferably by an accessory mounting pin and/or stage system(s), whereby with nestled said mobile processing device in said mobile processing device housing segment, said mobile processing device's camera lens(es) is unobstructedly coaxial with the optical axis of at least one from said group comprising subject's central cornea, tear-film layer(s), and target source(s).

38. The method of claim 17, whereby said ophthalmological instrument system configured to said mobile processing device can be removably fitted to a slit-lamp biomicroscope in a secure fashion, preferably by an accessory mounting pin and/or stage system(s), whereby with nestled said mobile processing device in said mobile processing device housing segment, said mobile processing device's camera lens(es) is unobstructedly coaxial with the optical axis of at least one from said group comprising subject's central cornea, tear-film layer(s), and target source(s).

39. The method of claim 19, whereby said ophthalmological instrument system configured to said mobile processing device can be removably fitted to a slit-lamp biomicroscope in a secure fashion, preferably by an accessory mounting pin and/or stage system(s), whereby with nestled said mobile processing device in said mobile processing device housing segment, said mobile processing device's camera lens(es) is unobstructedly coaxial with the optical axis of at least one from said group comprising subject's central cornea, tear-film layer(s), and target source(s).

40. The method of claim 20, whereby said ophthalmological instrument system configured to said mobile processing device can be removably fitted to a slit-lamp biomicroscope in a secure fashion, preferably by an accessory mounting pin and/or stage system(s), whereby with nestled said mobile processing device in said mobile processing device housing segment, said mobile processing device's camera lens(es) is unobstructedly coaxial with the optical axis of at least one from said group comprising subject's central cornea, tear-film layer(s), and target source(s).

41. The method of claim 21, whereby said ophthalmological instrument system configured to said mobile processing device can be removably fitted to a slit-lamp biomicroscope in a secure fashion, preferably by an accessory mounting pin and/or stage system(s), whereby with nestled said mobile processing device in said mobile processing device housing segment, said mobile processing device's camera lens(es) is unobstructedly coaxial with the optical axis of at least one from said group comprising subject's central cornea, tear-film layer(s), and target source(s).

42. The method of claim 23, whereby said ophthalmological instrument system configured to said mobile processing device can be removably fitted to a slit-lamp biomicroscope in a secure fashion, preferably by an accessory mounting pin and/or stage system(s), whereby with nestled said mobile processing device in said mobile processing device housing segment, said mobile processing device's camera lens(es) is unobstructedly coaxial with the optical axis of at least one from said group comprising subject's central cornea, tear-film layer(s), and target source(s).

43. The method of claim 27, whereby said ophthalmological instrument system configured to said mobile processing device can be removably fitted to a slit-lamp biomicroscope in a secure fashion, preferably by an accessory mounting pin and/or stage system(s), whereby with nestled said mobile processing device in said mobile processing device housing segment, said mobile processing device's camera lens(es) is unobstructedly coaxial with the optical axis of at least one from said group comprising subject's central cornea, tear-film layer(s), and target source(s).

44. The method of claim 29, whereby said ophthalmological instrument system configured to said mobile processing device can be removably fitted to a slit-lamp biomicroscope in a secure fashion, preferably by an accessory mounting pin and/or stage system(s), whereby with nestled said mobile processing device in said mobile processing device housing segment, said mobile processing device's camera lens(es) is unobstructedly coaxial with the optical axis of at least one from said group comprising subject's central cornea, tear-film layer(s), and target source(s).

45. The method of claim 31, whereby said ophthalmological instrument system configured to said mobile processing device can be removably fitted to a slit-lamp biomicroscope in a secure fashion, preferably by an accessory mounting pin and/or stage system(s), whereby with nestled said mobile processing device in said mobile processing device housing segment, said mobile processing device's camera lens(es) is unobstructedly coaxial with the optical axis of at least one from said group comprising subject's central cornea, tear-film layer(s), and target source(s).

\* \* \* \* \*